US012639796B2

(12) United States Patent (10) Patent No.: US 12,639,796 B2

Takahashi (45) Date of Patent: May 26, 2026

(54) IMAGE PROCESSING APPARATUS, RADIATION IMAGING SYSTEM, IMAGE PROCESSING METHOD, AND COMPUTER-READABLE MEDIUM

(71) Applicant: CANON KABUSHIKI KAISHA, Tokyo (JP)

(72) Inventor: Naoto Takahashi, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 748 days.

(21) Appl. No.: 17/898,519

(22) Filed: Aug. 30, 2022

(65) Prior Publication Data

US 2023/0070520 A1 Mar. 9, 2023

(30) Foreign Application Priority Data

Sep. 7, 2021 (JP) ................................. 2021-145495

(51) Int. Cl.
*G06T 5/77* (2024.01)
*A61B 6/00* (2024.01)

(52) U.S. Cl.
CPC .............. *G06T 5/77* (2024.01); *A61B 6/5258* (2013.01)

(58) Field of Classification Search
None
See application file for complete search history.

(56) References Cited

U.S. PATENT DOCUMENTS

| | | | |
|---|---|---|---|
| 8,837,516 B2 | 9/2014 | Umehara et al. | |
| 2003/0016854 A1* | 1/2003 | Inoue ..................... | H04N 25/68 |
| | | | 348/E5.081 |
| 2010/0266187 A1* | 10/2010 | Crucs ..................... | H04N 23/81 |
| | | | 382/275 |
| 2019/0050970 A1* | 2/2019 | Cresens ................... | G06T 5/77 |
| 2021/0133979 A1 | 5/2021 | Takahashi | |
| 2022/0189141 A1 | 6/2022 | Takahashi | |

FOREIGN PATENT DOCUMENTS

| | | | |
|---|---|---|---|
| JP | H10150571 A | * | 6/1998 |
| JP | 2002330341 A | | 11/2002 |
| JP | 2003-037777 A | | 2/2003 |
| JP | 2009-188624 A | | 8/2009 |
| JP | 2011-166422 A | | 8/2011 |
| JP | 2012-029720 A | | 2/2012 |
| JP | 2012029826 A | | 2/2012 |

(Continued)

OTHER PUBLICATIONS

Notice of Reasons for Refusal issued by the Japanese Patent Office on Oct. 3, 2023 in corresponding JP Patent Application No. 2021-145495, with English translation.

*Primary Examiner* — Vincent Rudolph
(74) *Attorney, Agent, or Firm* — Carter, DeLuca & Farrell LLP

(57) ABSTRACT

Provided is an imaging processing apparatus including a first correcting unit configured to correct, in a case where a first pixel group continuing to a first defect pixel in an image includes a second defect pixel, a value of the second defect pixel by using values of a second pixel group continuing to the second defect pixel, and a second correcting unit configured to correct a value of the first defect pixel by using values of the first pixel group including a value corrected by the first correcting unit.

18 Claims, 12 Drawing Sheets

(56) References Cited

FOREIGN PATENT DOCUMENTS

| | | | |
|---|---|---|---|
| JP | 2013-146537 | A | 8/2013 |
| JP | 2017-060737 | A | 3/2017 |
| JP | 2020-048836 | A | 4/2020 |
| JP | 2020-088654 | A | 6/2020 |
| WO | 2009/157217 | A1 | 12/2009 |

* cited by examiner

FIG. 9A
| 5 | 4 | 3 | 4 | 5 |
|---|---|---|---|---|
| 4 | 2 | 1 | 2 | 4 |
| 3 | 1 | × | 1 | 3 |
| 4 | 2 | 1 | 2 | 4 |
| 5 | 4 | 3 | 4 | 5 |
FIG. 9B
901
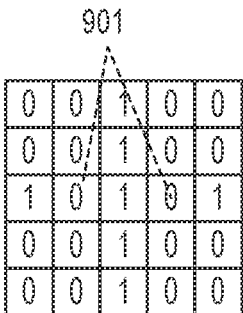
FIG. 9C
902
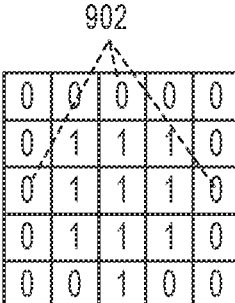

IDENTIFICATION RANGE OF DEFECT PIXEL

FIG. 12A
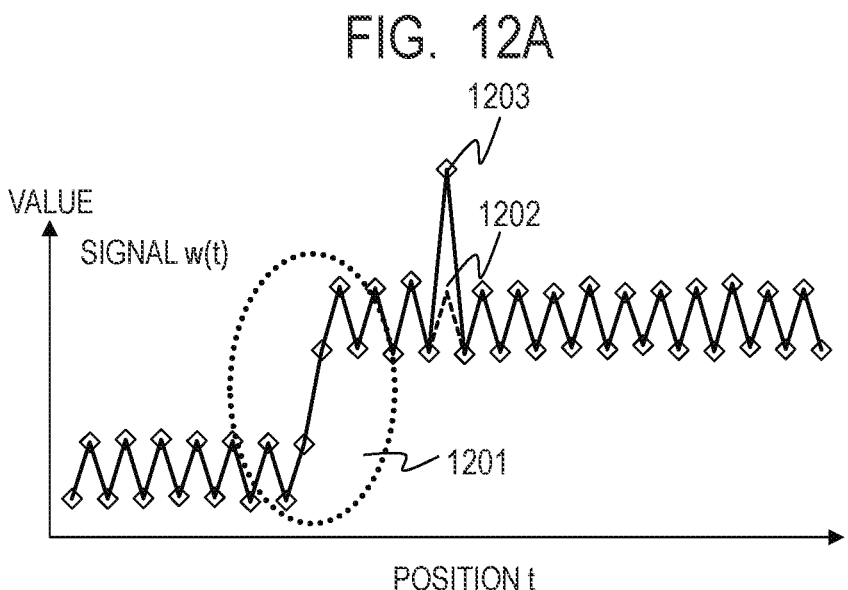
VALUE
SIGNAL w(t)
1203
1202
1201
POSITION t
FIG. 12B
VALUE
INTERPOLATED SIGNAL I(t)
POSITION t
FIG. 12C
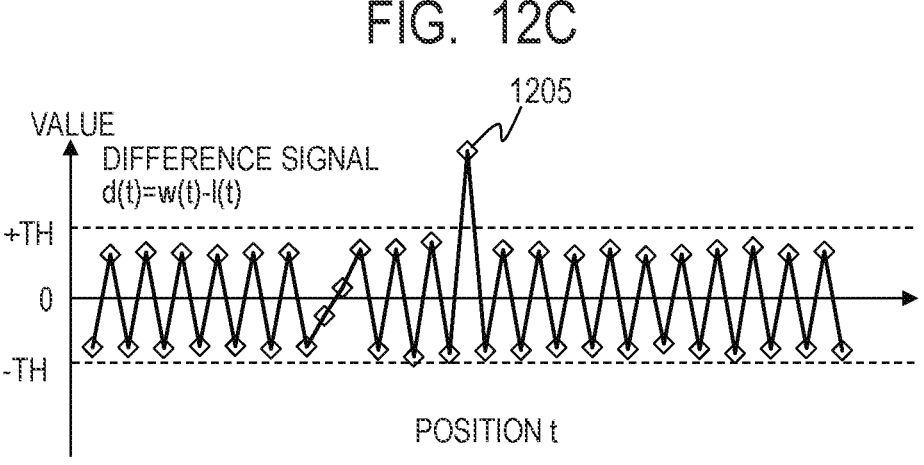
VALUE
DIFFERENCE SIGNAL
d(t)=w(t)-I(t)
1205
+TH
0
-TH
POSITION t

IMAGE PROCESSING APPARATUS, RADIATION IMAGING SYSTEM, IMAGE PROCESSING METHOD, AND COMPUTER-READABLE MEDIUM

BACKGROUND OF THE INVENTION

Field of the Invention

The present disclosure relates to an image processing apparatus, a radiation imaging system, an image processing method of the image processing apparatus, and a computer-readable medium.

Description of the Related Art

A radiation imaging system using a radiation detector called a flat panel detector (FPD) formed of a semiconductor material is known as an imaging system used for a medical image diagnosis. Such a radiation imaging system is used in the medical field as a digital imaging system for imaging a radiation transmitted through a subject.

In a plurality of pixels arranged in an FPD, there may be a pixel (hereinafter referred to as defect pixel) which always outputs an abnormal signal due to a problem in a manufacturing process of the FPD or the like. Since such a defect pixel causes an abnormal value in a captured image, correction processing called a defect correction is generally performed. It should be noted that the simplest method of the defect correction is interpolation using values of surrounding normal pixels, but this method cannot recover a signal component having a frequency which is ½ or more of the Nyquist frequency.

Japanese Patent Application Laid-Open No. 2002-330341 discloses a method for estimating a value of the defect pixel from statistical properties in pixels surrounding the defect pixel by a prediction analysis. This method can predict a signal component including a grid signal with high accuracy even in captured data in which a high frequency component of a grid stripe or the like is superimposed. Japanese Patent Application Laid-Open No. 2012-29826 discloses a method for predicting and restoring a grid stripe based on pixel values inside and outside the defect pixel.

However, the method disclosed in Japanese Patent Application Laid-Open No. 2002-330341 assumes that the defect pixel has a width of 1 pixel, and does not consider a case where the defect pixels become a large lump or are densely packed in the periphery. Therefore, the method described in Japanese Patent Application Laid-Open No. 2002-330341 has a problem that the prediction accuracy deteriorates in such a case.

The method disclosed in Japanese Patent Application Laid-Open No. 2012-29826 can correct the defect pixel even if the defect pixels become a large lump. However, the method uses a relationship between a pixel pitch and a period of the grid. Therefore, the method disclosed in Japanese Patent Application Laid-Open No. 2012-29826 has a problem that the prediction accuracy deteriorates if the relationship breaks under an influence of manufacturing variations, in-plane variations, mounting angles, and the like of the grid. Further, the method disclosed in Japanese Patent Application Laid-Open No. 2012-29826 is based on the prediction of the grid stripe, and has a problem that a high frequency component other than that of the grid stripe cannot be restored.

SUMMARY OF THE INVENTION

An exemplary object of an aspect of the present disclosure is to provide an image processing apparatus can perform accurate correction of the values of the defect pixels using the prediction analysis even if the defect pixels are densely packed.

An image processing apparatus according to an aspect of the present disclosure includes: a first correcting unit configured to correct, in a case where a first pixel group continuing to a first defect pixel in an image includes a second defect pixel, a value of the second defect pixel by using values of a second pixel group continuing to the second defect pixel, and a second correcting unit configured to correct a value of the first defect pixel by using values of the first pixel group including a value corrected by the first correcting unit.

Further features of the present invention will become apparent from the following description of exemplary embodiments with reference to the attached drawings.

BRIEF DESCRIPTION OF THE DRAWINGS

FIG. 9A is a diagram for explaining a defect correction by interpolation.

FIG. 9B is a diagram for explaining the defect correction by the interpolation.

FIG. 9C is a diagram for explaining the defect correction by the interpolation.

FIG. 12A is a diagram for explaining the prediction analysis.

FIG. 12B is a diagram for explaining the prediction analysis.

FIG. 12C is a diagram for explaining the prediction analysis.

DESCRIPTION OF THE EMBODIMENTS

Exemplary embodiments of the present disclosure will now be described in detail in accordance with the accompanying drawings.

First Embodiment

Figure 1:
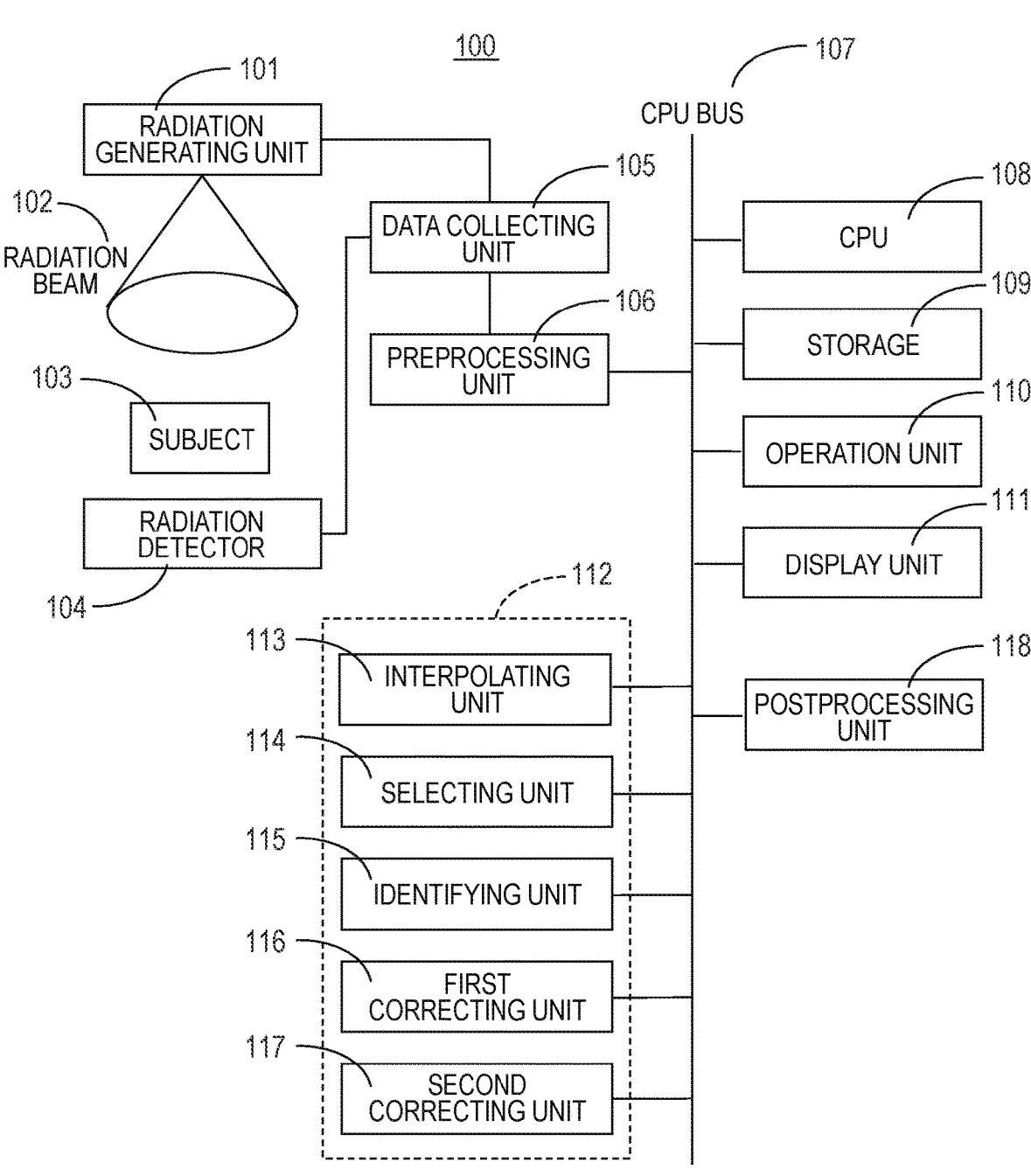
FIG. 1 is a diagram for illustrating a configuration example of a radiation imaging system.

FIG. 1 is a diagram for illustrating a configuration example of a radiation imaging system 100 according to a first embodiment of the present disclosure. The radiation imaging system 100 has an image processing function of correcting a defect pixel from an image obtained by radiation imaging. The radiation imaging system 100 includes a radiation generating unit 101, a radiation detector 104, a data collecting unit 105, a preprocessing unit 106, a CPU 108, a storage 109, an operation unit 110, a display unit 111, an image processing apparatus 112, and a postprocessing unit 118. These components can exchange data with each other via a CPU bus 107.

The image processing apparatus 112 corrects the defect pixel from an image captured by the radiation detector 104, and includes an interpolating unit 113, a selecting unit 114, an identifying unit 115, a first correcting unit 116, and a second correcting unit 117.

The storage 109 stores various data necessary for processing by the CPU 108 and functions as a working memory of the CPU 108. The CPU 108 uses the storage 109 to control an operation of the radiation imaging system 100 in accordance with an operation from the operation unit 110. As a result, the radiation imaging system 100 operates as follows.

First, an operator selects a desired one of a plurality of imaging protocols through the operation unit 110, and an imaging instruction is performed on the radiation imaging system 100. Here, the imaging protocol is a series of operation parameter sets used when performing a desired inspection, and it is possible to easily set conditions according to the inspection by preparing the plurality of imaging protocols in advance. Various settings such as an imaged site, an imaging-condition (tube voltage, tube current, irradiation time, etc.) and image processing parameters are associated with information of the imaging protocol.

The imaging instruction inputted by the operator as described above is transmitted to the data collecting unit 105 by the CPU 108. Upon receiving the imaging instruction, the CPU 108 controls the radiation generating unit 101 and the radiation detector 104 to cause them to execute the radiation imaging.

In the radiation imaging, the radiation generating unit 101 irradiates radiation beam 102 with respect to the subject 103. The radiation beam 102 irradiated from the radiation generating unit 101 is attenuated through the subject 103 and reaches the radiation detector 104. Then, the radiation detector 104 outputs a signal corresponding to an intensity of the reached radiation. Note that, in the first embodiment, the subject 103 is a human body. Therefore, the signal output from the radiation detector 104 is data obtained by imaging the subject 103.

The data collecting unit 105 converts the signal output from the radiation detector 104 into a predetermined digital signal and supplies it to the preprocessing unit 106 as image data. The preprocessing unit 106 performs preprocessing such as offset correction and a gain correction on the image data supplied from the data collecting unit 105. The CPU 108 transfers the image data preprocessed by the preprocessing unit 106 to the image processing apparatus 112 via the CPU bus 107.

The image processing apparatus 112 performs image processing for correcting a value of a defect pixel existing in the transferred image data, and stores an image to which the image processing is performed in storage 109. The postprocessing unit 118 performed various processes, such as gradation processing and enhancement processing, in order to make the image processed by the image processing apparatus 112 more suitable for diagnosis. The display unit 111 displays the image processed by the postprocessing unit 118.

After the operator checks the displayed image of the display unit 111, the CPU 108 outputs the image to a printer (not shown) or the like, and ends a series of the imaging operations.

Next, the operation of the image processing apparatus 112, that is, the operation of correcting the value of the defect pixel existing in the captured image data, will be described.

Figure 8A:
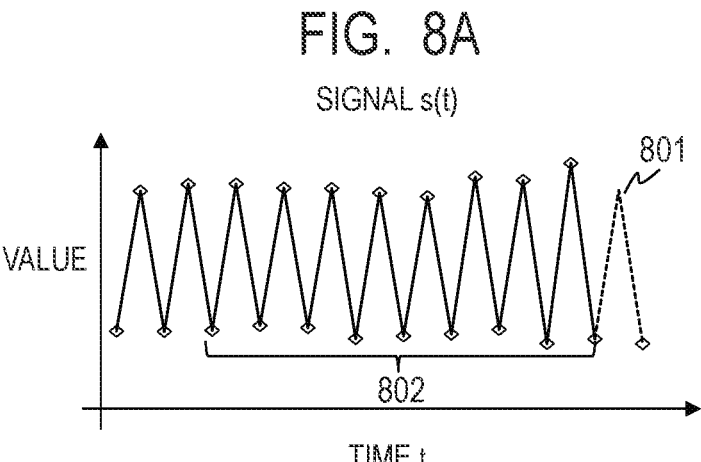
FIG. 8A is a diagram for explaining a prediction analysis.

Before a description of the correction, a description will be given of a prediction analysis using an autoregressive model (also called an AR model) used in the first embodiment. The prediction analysis with the autoregressive model is a method for predicting a future signal value (unknown) by a linear map using the past signal value (known). For example, for a signal s(t) shown in FIG. 8A, the prediction analysis predicts a future signal value 801 by using a past signal value 802. The model is expressed by the following expression (1).

$$s(t) + \sum_{i=1}^{n} a_{n,i} \cdot s(t-i) = e(t) \tag{1}$$

In the expression (1), $a_{n,\,i}$ is an n-th order AR coefficient (prediction coefficient), and e(t) represents a white noise. If it is possible to calculate the AR coefficient such that e(t) becomes 0, then the expression (1) becomes the following expression (2). The expression (2) can be used to predict the signal s(t) at time t by the linear sum of known signals s(t−1), s(t−2), . . . , s(t−n) prior to time t and the AR coefficient.

$$s(t) = -\sum_{i=1}^{n} a_{n,i} \cdot s(t-i) \tag{2}$$

Note that in the expression (2), it is necessary to calculate the AR coefficient by which e(t) becomes 0. A calculation method of the AR coefficient will be described later.

Figure 8B:
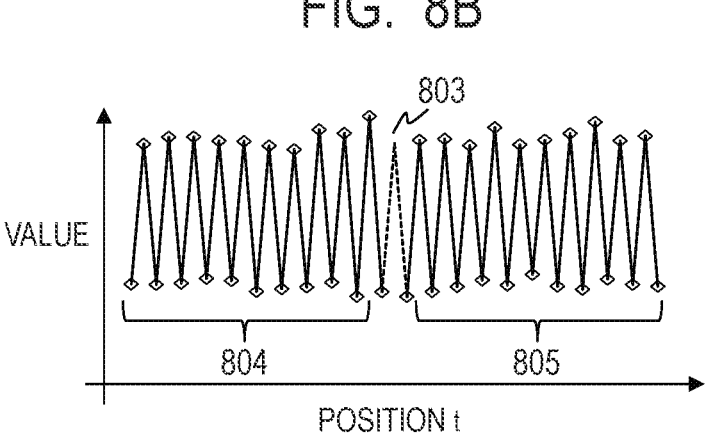
FIG. 8B is a diagram for explaining the prediction analysis.

Here, in a case where the prediction analysis described above is performed on an image, the same operation can be performed if, with respect to the image data of the two-dimensional array, data continuous in any of a row direction, a column direction, and a diagonal direction is considered as the one-dimensional signal s(t). For example, as shown in FIG. 8B, if the defect pixel 803 is set as the center and sample data in any of those directions is extracted, an AR coefficient can be calculated from known pixel value around the defect pixel 803. In a case of the image data, since a forward sample 804 and a backward sample 805 are known with respect to the position of the defect pixel 803 as the center, the AR coefficient can be determined by using any of the samples.

Figure 8C:
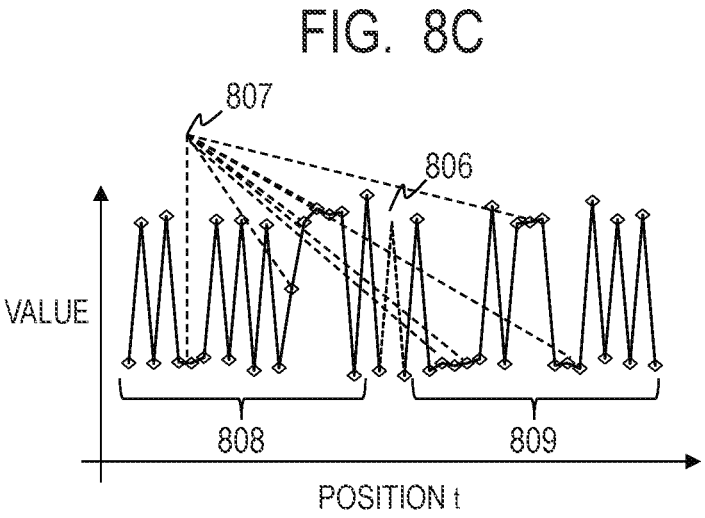
FIG. 8C is a diagram for explaining the prediction analysis.

Note that FIG. 8B is a diagram for illustrating a case where the values of pixels around the defect pixel 803 are known (a case where the pixels are normal pixels). By contrast, if a pixel around the defect pixel is also a defect pixel, the value of pixel used for the prediction is different from a pristine value. For example, FIG. 8C shows this state. In FIG. 8C, in addition to a defect pixel 806, there are also defect pixels 807 around the defect pixel 806. The values of the defect pixels 807 are different from pristine values shown in FIG. 8B. In this case, the signal waveform is different from a pristine signal waveform, and the prediction accuracy decreases.

Therefore, in the first embodiment, in a case where there is a defect pixel among the pixels used for prediction, such a pixel is predicted first, the signal waveform is approximated to the pristine waveform, and then the prediction analysis of the defect pixel, which is a correction target, is performed, in order to suppress the deterioration of the prediction accuracy.

Figure 2:
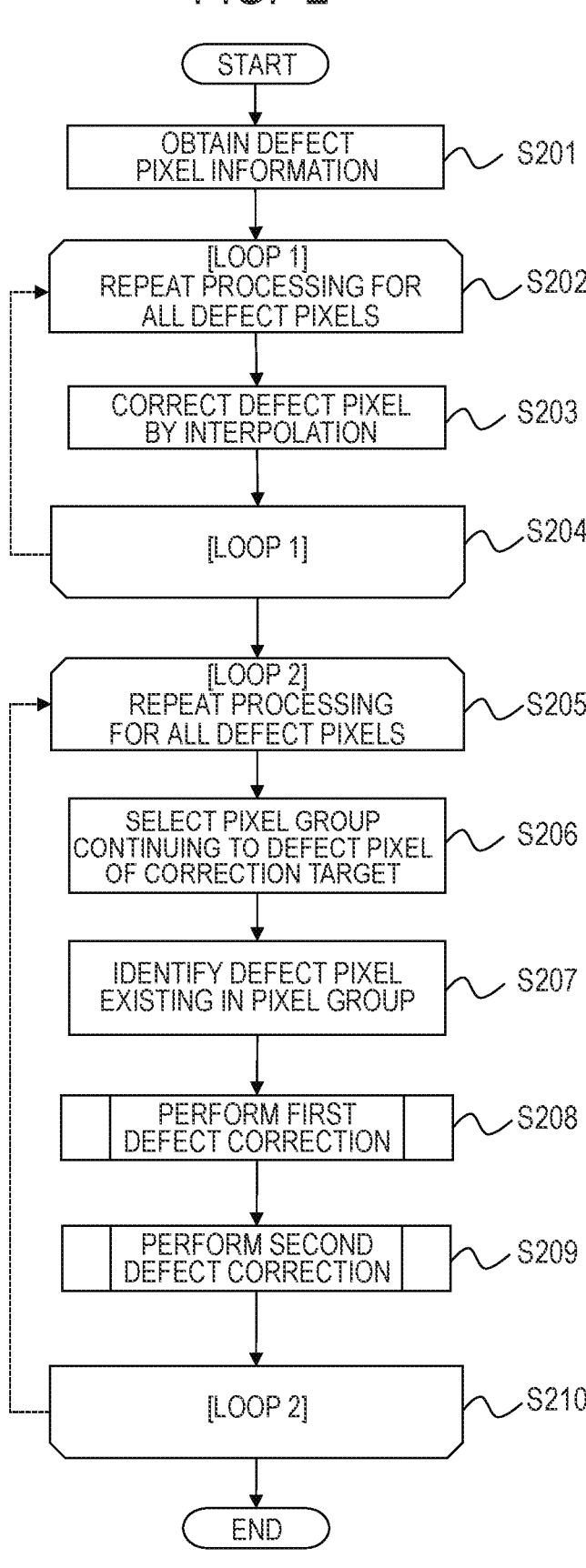
FIG. 2 is a flowchart showing an image processing method of an image processing apparatus.

Based on the above, the correction operation according to the first embodiment will be specifically described with reference to the flowcharts shown in FIG. 2 to FIG. 5. FIG. 2 is a flowchart showing the image processing method of the image processing apparatus 112. As described above, the CPU 108 transfers the image data obtained by the preprocessing unit 106 to the image processing apparatus 112 via the CPU bus 107.

In step S201, the interpolating unit 113 obtains the image data, and obtains defect pixel information held in the storage 109 in advance. Here, the defect pixel is detected in advance by factory inspection before shipment. The storage 109 holds the detected defect pixel information. A data format of the defect pixel information is not particularly limited, but is, for example, binary image data (hereinafter referred to as defect map) in the same matrix as the image data, where the defect pixel is set to 1 and the normal pixel is set to 0.

Next, in step S202, the interpolating unit 113 repeats the loop processing of steps S202 to S204 for all defect pixels. In step S203, the interpolating unit 113 corrects the value of the defect pixel by interpolation. This correction is a provisional defect correction. The interpolating unit 113 corrects, with respect to the values of all pixels (defect pixels) of which values are 1 in the defect map, the value of the defect pixel by interpolating values of pixels (normal pixels), of which values are 0 in the defect map, around the defect pixel. The specific interpolation method is not particularly limited.

For example, the interpolating unit 113 corrects the value of the defect pixel by means of the average (linear interpolation) of the values of the normal pixels that have the same distance from the defect pixel. Specifically, as shown in FIG. 9A, in a case where the defect pixel as a correction target is represented by X, the interpolating unit 113 sorts pixels belonging to the same distance with respect to the defect pixel (pixels denoted by the same number in the FIG. 9A) into respective groups. Then, the interpolating unit 113 determines whether or not there is a normal pixel in order from pixels close to the defect pixel. If there is a normal pixel, the interpolating unit 113 uses the average value of values of the group of the normal pixels as the correction value of the defect pixel. For example, in a defect map according to the example shown in FIG. 9B, since there are two normal pixels 901 having a distance of 1, the interpolating unit 113 uses the average value of the values of the two normal pixels 901 as the correction value of the defect pixel. On the other hand, in a defect map according to the example shown in FIG. 9C, since there is no normal pixel having distance of 1 or 2 and three normal pixel 902 having distance of 3, the interpolating unit 113 uses the average value of the values of these three pixels as the correction value of the defect pixel. In FIG. 9A to FIG. 9C, the images are represented by a 5×5 matrix, but the interpolating unit 113 can search a larger area and perform the provisional correction for the defect pixels which are a large lump.

Next, the image processing apparatus 112 executes the loop processing of steps S205 to S210 to perform a defect correction by a prediction analysis. Specifically, the image processing apparatus 112 executes the processing in steps S206 to S209 for all defect pixels. Note that the image processing apparatus 112 uses the image corrected by the interpolating unit 113 as an input, temporarily stores the correction result of the defect pixel in a working memory of the storage 109, and updates the input data after all defect pixels have been corrected.

Figures 10A, 10B:
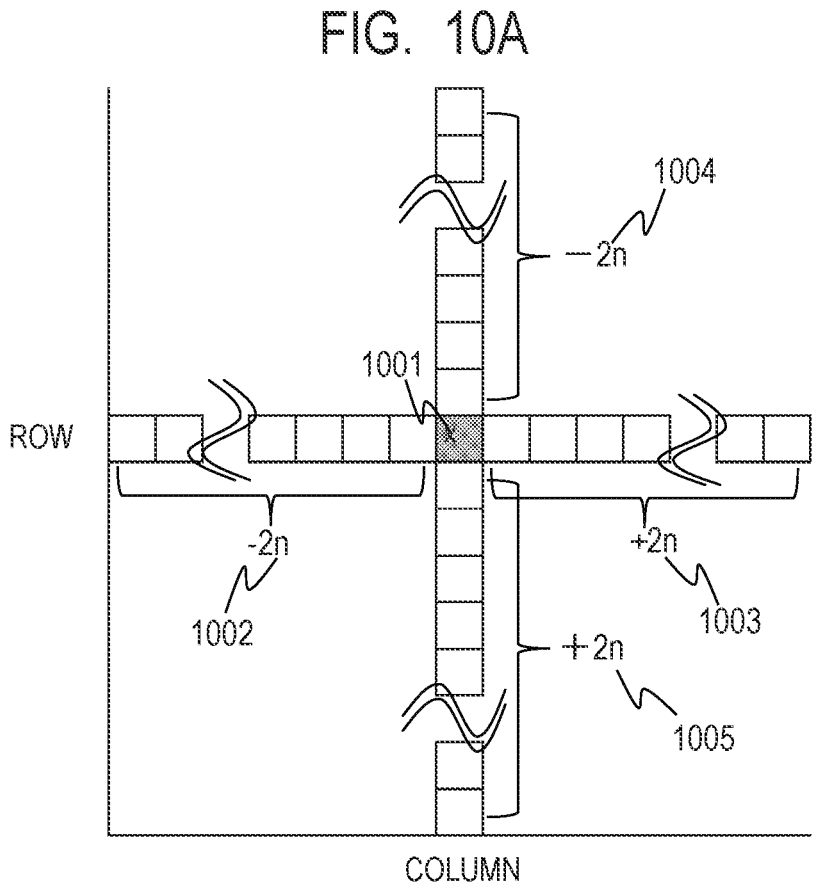
FIG. 10A is a diagram for explaining an operation of a selecting unit.
FIG. 10B is a diagram for explaining the operation of the selecting unit.

Operation for one defect pixel will be described below. First, in step S206, the selecting unit 114 selects a pixel group to be used for a prediction of the defect pixel as a target. As described above, the pixel group used for the prediction may be data continuous in any of a row direction, a column direction, and a diagonal direction. In the first embodiment, the selecting unit 114 selects data in a direction, in which the number of defect pixels is fewer, between the row direction and the column direction. As shown in FIG. 10A, in a case where the number of samples to be used for the prediction of the defect pixel 1001 as the correction target is n, the selecting unit 114 extracts, as sample data, forward 2n pixels 1002 and backward 2n pixels 1003 in the column direction with respect to the defect pixel 1001 at the center. In addition, the selecting unit 114 extracts, as sample data, forward 2n pixels 1004 and backward 2n pixels 1005 in the row direction with respect to the defect pixel 1001 at the center. The selecting unit 114 compares the number of defect pixels existing in the sample data in both directions, and stores the sample data having the fewer defect pixels in the working memory of the storage 109 as a pixel group v(t) used for the prediction. The number n of the samples used for the prediction may be empirically determined in consideration of processing time, etc., and n=20 in the first embodiment.

Next, in step S207, the identifying unit 115 identifies a position of the defect pixel existing in the pixel group v(t) selected by the selecting unit 114. As shown in FIG. 10B, the identifying unit 115 defines ranges of forward n pixels and backward n pixels of the defect pixel 1006 as identification ranges of the defect pixel, and generates a data row of the defect map (defect pixel is set to 1, and normal pixel is set to 0) corresponding to the pixel group v(t) from the defect map. The ranges of the forward n pixels and the backward n pixels of the defect pixel 1006 is a range of the sample data used for the prediction.

Figure 3:
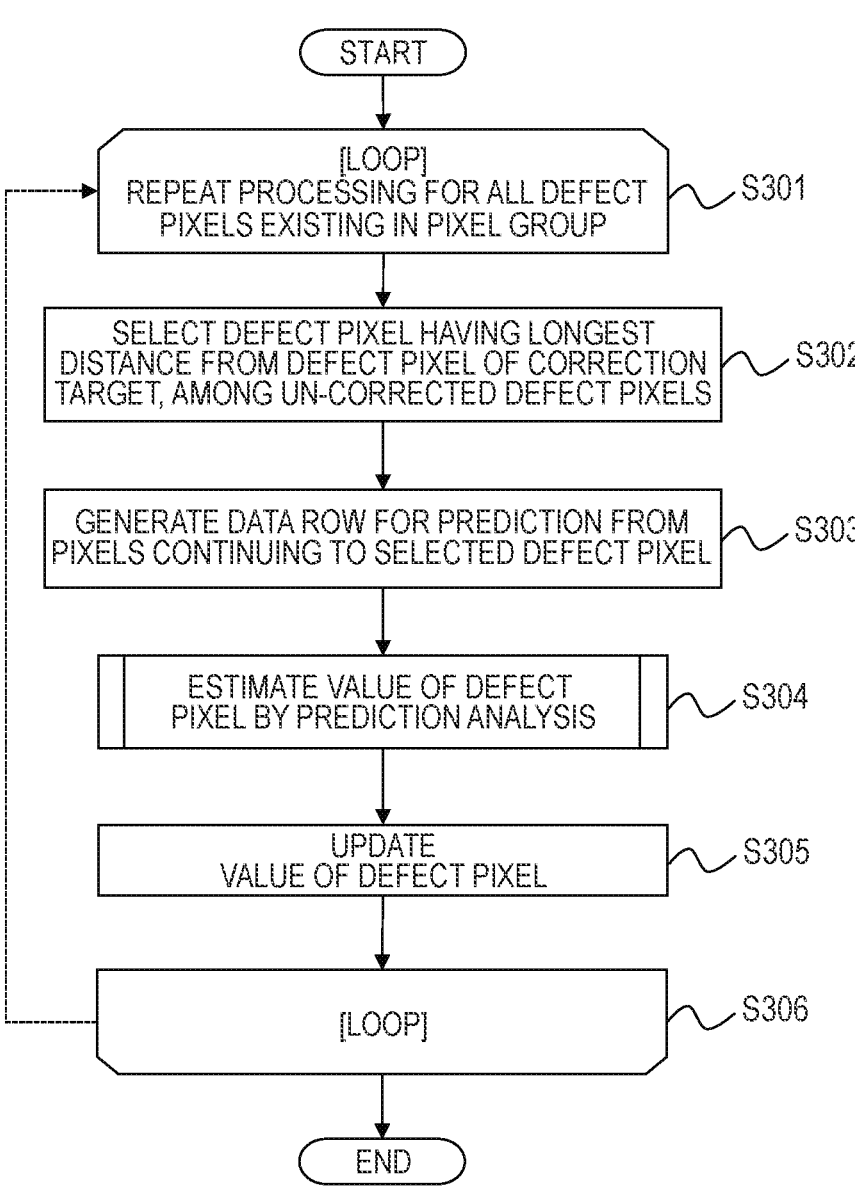
FIG. 3 is a flowchart showing a processing procedure of first defect correction.

Next, in step S208, the first correcting unit 116 performs the defect correction of a pixel that is represented as the defect pixel (the value is 1) in the data row of the defect map generated by the identifying unit 115. FIG. 3 is a flowchart showing the details of step S208.

First, as shown in FIG. 10B, the first correcting unit 116 corrects the values of the defect pixels by executing the loop processing in steps S301 to S306 for all pixels that exist in the pixel group v(t) and are represented as the defect pixels (the value is 1) with reference to the data row of the defect map.

Figure 11A:
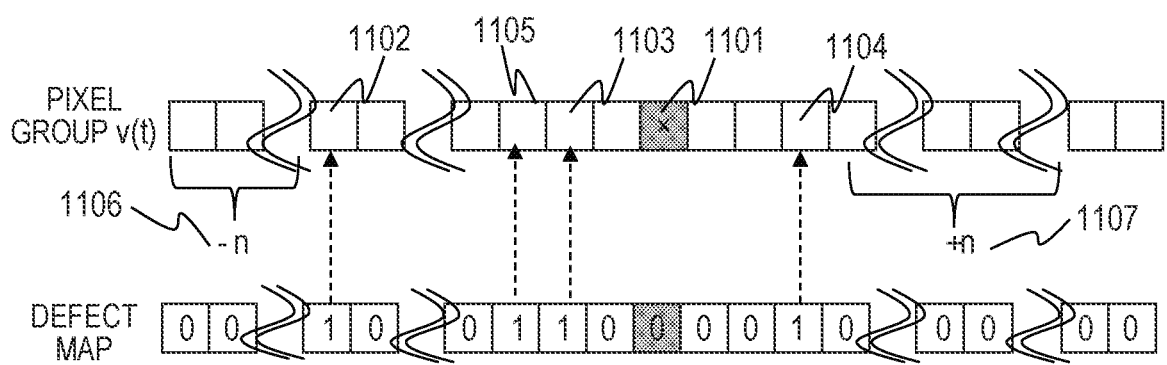
FIG. 11A is a diagram for explaining an operation of a first correcting unit.

First, in step S302, the first correcting unit 116 selects a pixel that is farthest from the defect pixel as the correction target among uncorrected defect pixels existing in the pixel group v(t). For example, as shown in FIG. 11A, in a case where there are uncorrected defect pixels 1102, 1103, 1104, 1105 with respect to a defect pixel 1101 as the correction target, the first correcting unit 116 selects a defect pixel 1102 farthest from the defect pixel 1101. Note that, in a case where two farthest pixels which are separated by the same distance on the left and right sides exist such as the defect pixels 1104 and 1105, the first correcting unit 116 may select either pixel.

Next, in step S303, the first correcting unit 116 generates a data row for the prediction from pixels continuing (connected) to the selected defect pixel. The first correcting unit

116 generates, as the data row for the prediction, pixels that continue in a direction opposite to a direction in which the defect pixel as the correction target exists with respect to the selected defect pixel. In a case where the defect pixel 1102 in FIG. 11A is the selected defect pixel, the first correcting unit 116 generates a pixel group 1106 of n pixels that range in a direction opposite to the defect pixel 1101 as the correction target with respect to the defect pixel 1102, that is, in the left direction, as the data row for the prediction. Further, in a case where the defect pixel 1104 is the selected defect pixel, the first correcting unit 116 generates a pixel group 1107 of n pixels continuing in the right direction as the data row for the prediction. In the following description, the generated data row w(t) is expressed as in the following expression (3).

$$w(t), t = 0, 1, 2, \ldots , n \tag{3}$$

Here, the data row w(t) is the generated data row. The data row w(t) represents pixel value at position t. Further, a value w(n) represents the value of the selected defect pixel 1102, and a value w(0) represents the value of the pixel farthest from the selected defect pixel 1102.

Figure 11B:
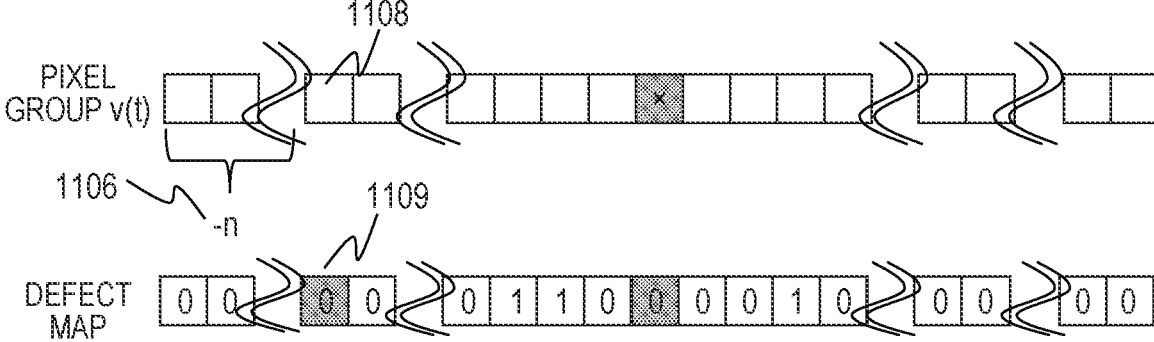
FIG. 11B is a diagram for explaining the operation of the first correcting unit.

Next, in step S304, the first correcting unit 116 performs the prediction analysis using the generated data row w(t) to estimate the value w(n) of the selected defect pixel 1102. In step S305, the first correcting unit 116 updates the value of the selected defect pixel 1102 to the determined estimated value w(n). For example, the first correcting unit 116, as shown in FIG. 11B, replaces the value of the selected defect pixel 1102 in the pixel group v(t) with the estimated value 1108, and also replaces the value 1109 in the defect map of the selected defect pixel 1102 with 0.

Figure 5:
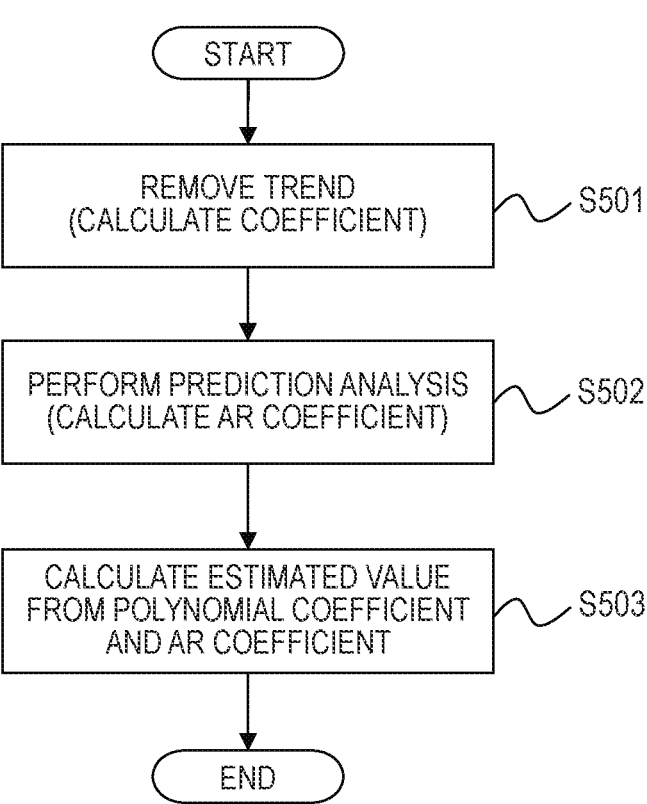
FIG. 5 is a flowchart showing a processing procedure of a prediction analysis.

FIG. 5 is a flowchart showing details of the prediction analysis in step S304 in FIG. 3. In step S501, the first correcting unit 116 generates a data row in which a trend component is removed from the generated data row w(t). Note that the removal of the trend component is not essential. The first correcting unit 116 performs the removal of the trend component as a preprocessing in order to stabilize the estimation of a prediction analysis. In the first embodiment, the first correcting unit 116 approximates data row w(t) by a linear expression and performs a subtraction to remove the trend component. Specifically, the first correcting unit 116 calculates polynomial coefficients A and B which minimize J in the expression (4), according to the expression (5).

$$J = \sum_{t=0}^{n} (w(t) - (A \cdot t + B))^2 \rightarrow \text{minimize} \tag{4}$$

$$A = \frac{s_2 \cdot s_1 - (n+1) \cdot s_{12}}{s_1 \cdot s_1 - (n+1) \cdot s_{11}}, B = \frac{s_2 - A \cdot s_1}{n+1} \tag{5}$$

$$s_1 = \sum_{i=0}^{n} t, s_2 = \sum_{t=0}^{n} s(t), s_{11} = \sum_{i=0}^{n} t^2, s_{12} = \sum_{i=0}^{n} t \cdot s(t)$$

Then, the first correcting unit 116 removes, as the trend component, an approximate expression (A·t+B) according to the determined polynomial coefficients A and B from the data row w(t) in accordance with the expression (6) to determine a data row s(t).

$$s(t) = w(t) - (A \cdot t + B), t = 0, 1, 2, \ldots , n \tag{6}$$

Next, in step S502, the first correcting unit 116 calculates an AR coefficient from the determined data row s(t). As explained at the beginning, the AR coefficient is $a_{n, i}$ in the expression (2). There are different ways to calculate the AR coefficient. In the first embodiment, the first correcting unit 116 calculates the AR coefficient by using the Burg method. In the Burg method, the first correcting unit 116 defines a forward prediction error $f_n(t)$ and a backward prediction error $b_n(t)$ with respect to the autoregressive model of the expression (2) as expressed by the expression (7), and calculates the AR coefficient $a_{n, i}$ in which the error function $J_n$ of the sum of squares thereof is minimized by solving the minimization problem.

$$J_n = \sum_{i=n+1}^{N} f_n^2(i) + \sum_{i=1}^{N-n} b_n^2(i) \rightarrow \text{minimize} \tag{7}$$

$$f_n(t) = s(t) + \sum_{i=1}^{n} a_{n,i} \cdot s(t-i), b_n(t) = s(t) + \sum_{i=1}^{n} a_{n,i} \cdot s(t+i)$$

Here, an n-th order AR coefficient $a_{n, i}$ and an n−1-th order AR coefficient $a_{n-1, i}$ are expressed by the expression (8) using the Levinson's recursion formula.

$$a_{n,i} = a_{n-1,i} + a_{n,n} \cdot a_{n-1,n-1} \tag{8}$$

An n-th order forward prediction error $f_n(t)$ and an n-th order backward prediction error $b_n(t)$, and an n−1-th order forward prediction error $f_{n-1}(t)$ and an n−1-th order backward prediction error $b_{n-1}(t)$ are expressed by the expression (9). Here, a coefficient $a_{n, n}$ is a coefficient called a reflection coefficient (or PARCOR coefficient). Using the relationship expressed by the expression (8), the n-th order AR coefficient can be determined from the reflection coefficient $a_{n, n}$.

$$f_n(t) = \begin{cases} f_{n-1}(t) + a_{n,n} \cdot b_{n-1}(t-n), n > 0 \\ s(t), \text{ otherwise} \end{cases} \tag{9}$$

$$b_n(t) = \begin{cases} b_{n-1}(t) + a_{n,n} \cdot f_{n-1}(t+n), n > 0 \\ s(t), \text{ otherwise} \end{cases}$$

The reflection coefficient an, n can be determined by substituting the error function $J_n$ shown in the expression (7) into the expression (9) and determining a value at which the partial differential of the expression becomes 0, that is, solving the following expression (10) for the reflection coefficient $a_{n, n}$.

$$\frac{\partial J_n}{\partial a_{n,n}} = \frac{\partial \sum_{k=n+1}^{N} (f_{n-1}(t) + a_{n,n} \cdot b_{n-1}(t-n))^2}{\partial a_{n,n}} +$$

$$\frac{\partial \sum_{k=1}^{N-n} (b_{n-1}(t) + a_{n,n} \cdot f_{n-1}(t+n))^2}{\partial a_{n,n}} = 0 \tag{10}$$

Solving the expression (10), the following expression (11) is obtained, and it is understood that an n-th order reflection coefficient an n can be estimated from the n−1-th order forward prediction error $f_{n-1}(t)$ and the n−1-th order backward prediction error $b_{n-1}(t-n)$.

$$a_{n,n} = -2 \cdot \frac{M_n}{D_n} \tag{11}$$

$$M_n = \sum_{t=n+1}^{N} f_{n-1}(t) \cdot b_{n-1}(t-n), \quad D_n = \sum_{t=n+1}^{N} \left( f_{n-1}^2(t) + b_{n-1}^2(t-n) \right) \tag{}$$

As described above, the first correcting unit 116 can recursively calculate an n-th order AR coefficient $a_{n, i}$ by using the relationships of the equations (8), (9), and (11).

Next, in step S503, the first correcting unit 116 calculates an estimated value using the obtained polynomial coefficients A, B and the AR coefficient $a_{n, i}$. The first correcting unit 116 calculates the value of the target defect pixel according to a prediction model as expressed by the expression (12), and then calculates the estimated value w(n) of the defect pixel by adding the removed trend component.

$$w(n) = \left( -\sum_{i=1}^{k} a_{k,i} \cdot s(n-i) \right) + (A \cdot n + B) \tag{12}$$

Here, k is the order of an AR coefficient $a_{k, i}$, and any order used for the prediction may be set to n or less. In the first embodiment, k=5.

Thus, in step S305 in FIG. 3, the first correcting unit 116 updates the calculated estimated value w(n) as the value of the defect pixel.

Next, in step S209 in FIG. 2, the second correcting unit 117 corrects the value of the defect pixel 1101 as the correction target by using the pixel group v(t) corrected by the first correcting unit 116.

Figure 4:
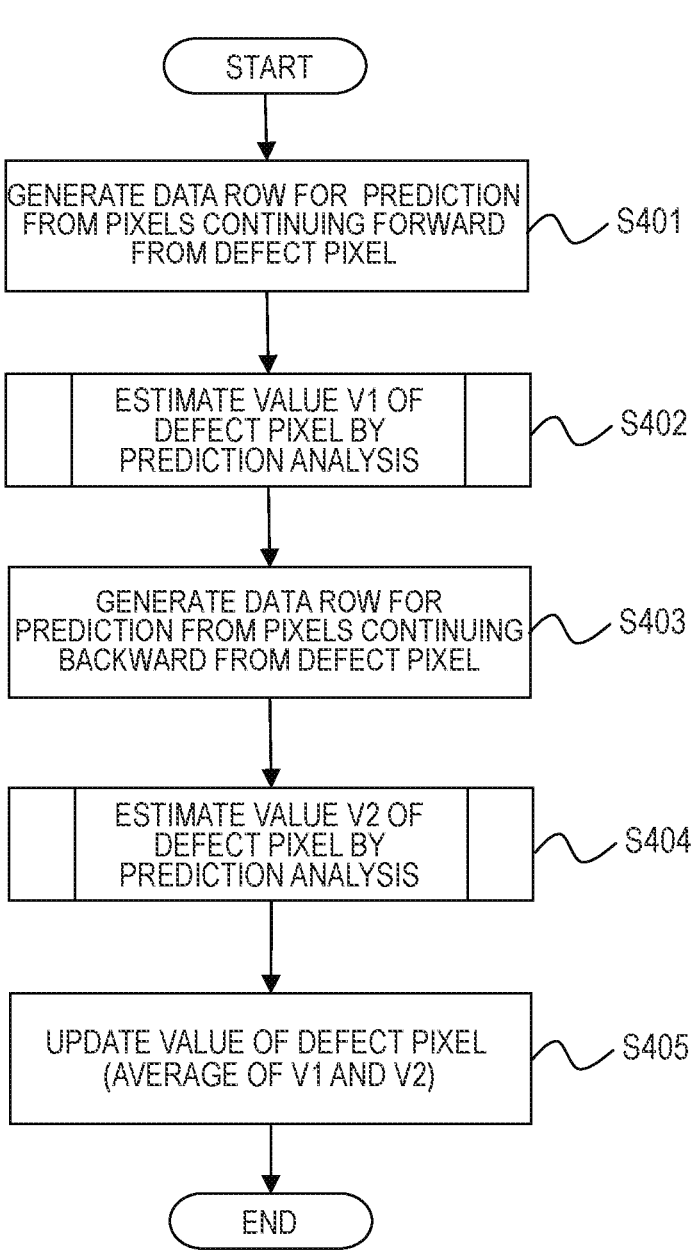
FIG. 4 is a flowchart showing a processing procedure of a second defect correction.

FIG. 4 is a flowchart showing the details of step S209 in FIG. 2. First, in step S401, the second correcting unit 117 generates a data row w(t) for a prediction from pixels continuing forward from the target defect pixel 1101. Specifically, the second correcting unit 117 generates the data row w(t) for the prediction from the pixel group 1008 of forward n pixels of the defect pixel 1006 as the correction target in FIG. 10B.

In step S402, the second correcting unit 117 calculates an estimated value V1 by a prediction analysis using the data row w(t) for the prediction. Here, the description of the prediction analysis is omitted because the processing is the same as that of the flowchart of FIG. 5 described above.

In step S403, as shown in FIG. 10B, the second correcting unit 117 generates a data row w(t) for a prediction from a pixel group 1009 of n pixels continuing backward from the target defect pixel 1006.

In step S404, the second correcting unit 117 calculates an estimated value V2 by a prediction analysis using the data row w(t) for the prediction.

In step S405, the second correcting unit 117 updates the value of defect pixel 1006 using the average of the two estimated values V1 and V2.

The image processing apparatus 112 performs the processing in steps S205 to S210 in FIG. 2 for all defect pixels, and thereby the defect correction is completed.

As mentioned above, the radiation detector 104 captures the image. In step S203 in FIG. 2, the interpolating unit 113 corrects the value of the defect pixel existing in the image by interpolation. The above-mentioned image is an image captured by using the radiation detector 104. In step S206, the selecting unit 114 selects first pixel groups 1008 and 1009 that continue to a first defect pixel 1006 existing in the image.

The selecting unit 114 selects, as the first pixel group, a pixel group that continues to a first defect pixel 1001 in any one of a row direction, a column direction, and a diagonal direction. For example, the selecting unit 114 selects, as the first pixel group, a pixel group in a direction in which the number of defect pixels existing in the pixel group is smaller between the pixel group continuing to the first defect pixel 1001 in the row direction and the pixel group continuing to the first defect pixel 1001 in the column direction.

In step S208, the first correcting unit 116 corrects the value of a second defect pixel 1102 if the second defect pixel 1102 exists in the first pixel groups 1008 and 1009. For example, the first correcting unit 116 corrects the value of the second defect pixel 1102 based on a prediction analysis by using values of a second pixel group 1106 continuing to the second defect pixel 1102.

The first correcting unit 116 corrects the value of the second defect pixel 1102 by using the values of the second pixel group 1106 continuing in a direction opposite to a direction in which the first defect pixel 1101 exist with respect to the second defect pixel 1102. There is a case in which a plurality of second defect pixels 1102 to 1105 exist in the first pixel groups 1008 and 1009. In this case, the first correcting unit 116 sequentially corrects the values of the second defect pixels in order from the second defect pixel farther from the first defect pixel 1101 among the plurality of second defect pixels 1102 to 1105.

In step S209, the second correcting unit 117 corrects, based on a prediction analysis, the value of the first defect pixel 1006 using values of the first pixel groups 1008 and 1009 including the value corrected by the first correcting unit 116. The first correcting unit 116 and the second correcting unit 117 perform the correction based on the image corrected by the interpolating unit 113.

The selecting unit 114 selects two or more first pixel groups 1008 and 1009. In this case, the second correcting unit 117 calculates two or more estimated values V1 and V2 of the first defect pixel 1006 using the values of the two or more first pixel groups 1008 and 1009, respectively, and corrects the value of the first defect pixel 1006 based on the two or more estimated values V1 and V2. For example, the second correcting unit 117 corrects the value of the first defect pixel 1006 with a value based on an average value or an order statistic of the two or more estimates V1 and V2.

In step S501 in FIG. 5, the first correcting unit 116 and the second correcting unit 117 respectively remove a trend from the values of the second pixel group and the values of the first pixel group, and perform the prediction analysis from the values from which the trend is removed. The trend removal is a process of approximating the values of the first pixel group or the second pixel group by a polynomial, and subtracting the approximate value from the values of the first pixel group or the second pixel group.

As described above, according to the first embodiment, if a defect pixel exists in pixels to be used for the prediction, the image processing apparatus 112 predicts such a pixel first, approximates the signal waveform to the pristine waveform, and then performs the prediction analysis of a defect pixel, which is correction target. Accordingly, deterioration in the prediction accuracy can be suppressed.

In the first embodiment, as shown in FIG. 10B, the range of pixels used for the prediction of the defect pixel 1006 is set to the ranges of forward n pixels and backward n pixels. However, there is a case where the prediction analysis is performed by referring to the pixels 1010 and 1011 in FIG. 10B, and if the pixels 1010 and 1011 are defect pixels, provisional values by the interpolation are referred to.

Therefore, if there is a defect pixel in this range, the prediction analysis may be sequentially performed by referring to pixels further outside. In this case, it is not necessary to perform the provisional correction by the interpolating unit 113. However, the effect of a defect pixel on the prediction coefficient decreases as a distance from the target defect pixel 1006 increases. Accordingly, as in the first embodiment, even if a provisional correction value by the interpolation is used, there is no significant effect and the number of times of sequential processing can be limited, and therefore it is also suitable from the viewpoint of processing time.

Second Embodiment

Figure 6:
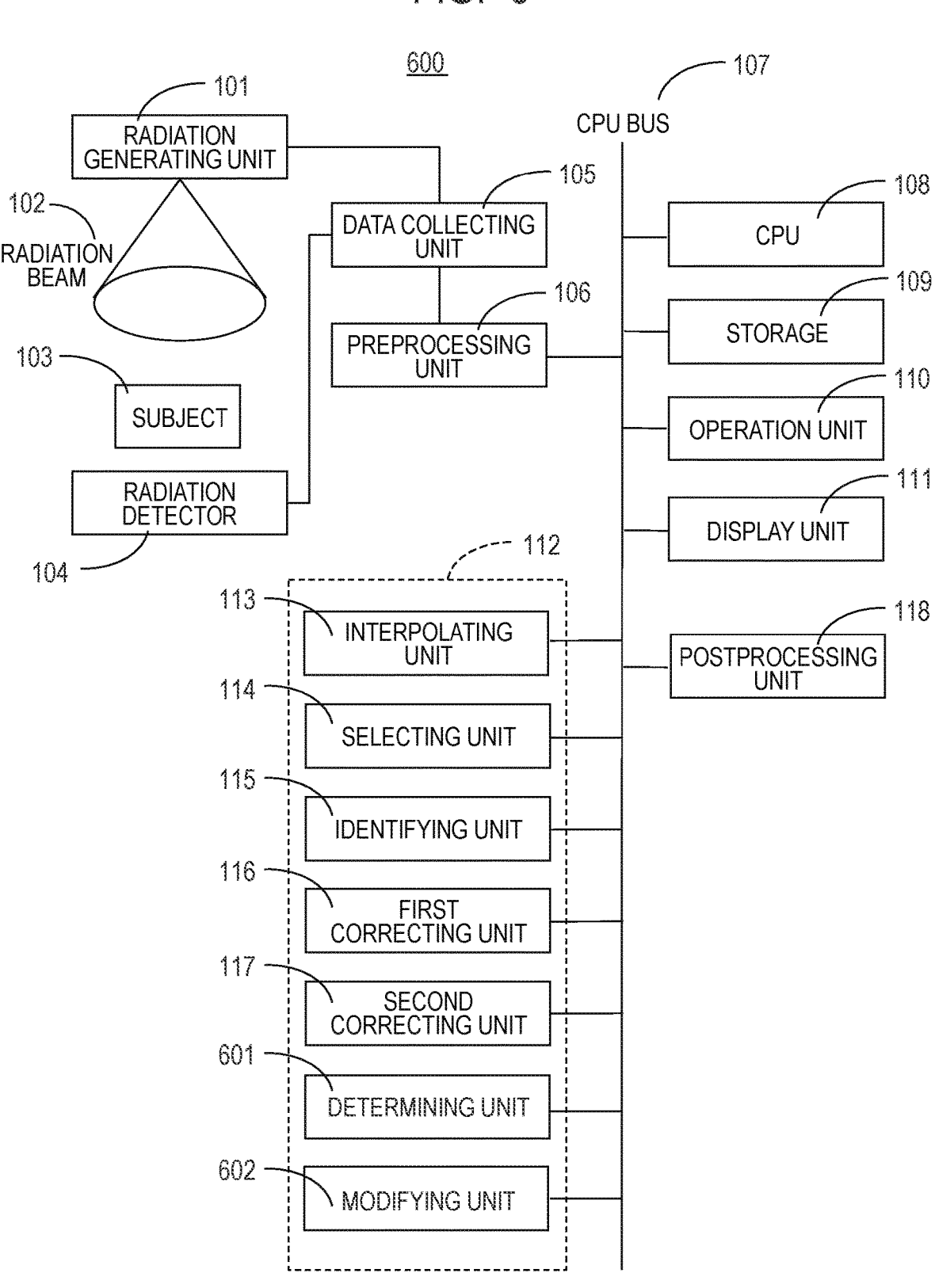
FIG. 6 is a diagram for illustrating a configuration example of a radiation imaging system.

FIG. 6 is a diagram illustrating for a configuration example of a radiation imaging system 600 according to the second embodiment. The radiation imaging system 600 is a system in which a determining unit 601 and a modifying unit 602 are added to the radiation imaging system 100 in FIG. 1. The image processing apparatus 112 has the determining unit 601 and the modifying unit 602. As a result, the image processing apparatus 112 determines validity of an estimated result of a prediction analysis and corrects the estimated result if it is not valid.

The second embodiment takes into account a case in which the prediction error is large in comparison with the first embodiment. Specifically, the prediction analysis assumes a steady signal, and the radiation imaging system 600 imaging a human body can be locally considered as almost steady. However, in a case where an implant or the like exists, a steep edge is generated on the image, and the above assumption may not be satisfied.

FIG. 12A shows a signal w(t) in which a steep edge 1201 is generated. In a case of such an unsteady signal w(t), a large error may occur between a pristine value 1202 and an estimated value 1203 based on the prediction. Therefore, in the second embodiment, in a case where there is a large difference between a value that can be estimated from a steady signal and the estimated value by the prediction, the image processing apparatus 112 determines that the value is not valid and corrects the estimated value.

The processing in which the second embodiment differs from the first embodiment will be described below. In the second embodiment, the processing of the prediction analysis described with reference to FIG. 5 in the first embodiment is different from that of the first embodiment, and the other processing is the same.

Figure 7:
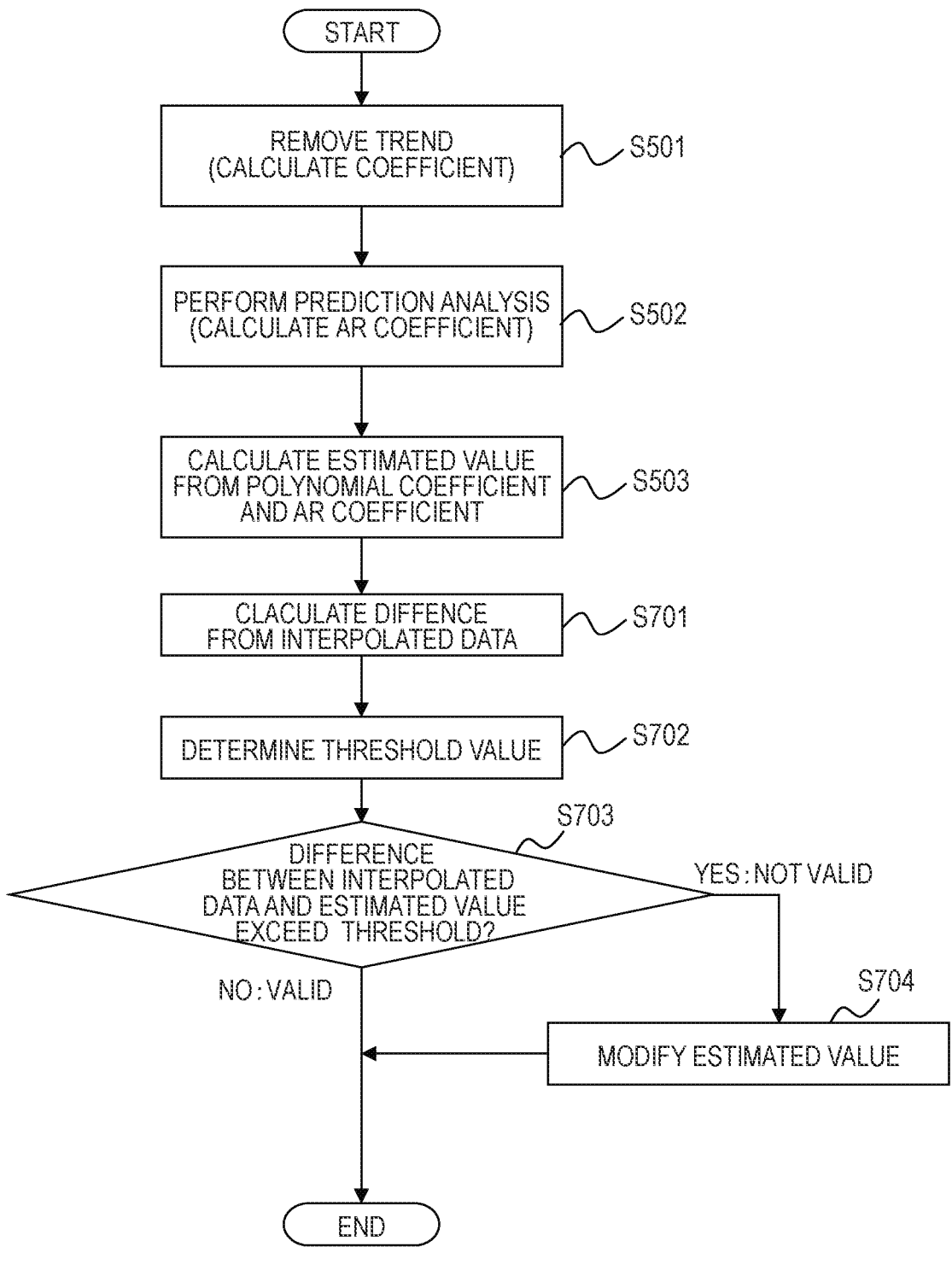
FIG. 7 is a flowchart showing a processing procedure of a prediction analysis.

FIG. 7 is a flowchart showing details of the prediction analysis in step S304 of FIG. 3. In FIG. 7, steps S701 to S704 are added to FIG. 5.

In steps S501 to S503, the first correcting unit 116 performs the same processing as in steps S501 to S503 in FIG. 5, and calculates the estimated value V.

Next, in steps S701 to S703, the determining unit 601 determines whether or not the estimated value V is valid. In step S701, the determining unit 601 calculates a difference signal d(t) between the signal w(t) and an interpolated signal l(t) in order to calculate a determination threshold. Specifically, as expressed by the expression (13), the determining unit 601 generates the interpolated signal l(t) in FIG. 12B in which the value of each pixel is replaced by the average value of values of pixels on the both sides with respect to the signal w(t) used for the prediction. The determining unit 601 calculates the difference signal d(t) shown in FIG. 12C by subtracting the interpolation signal l(t) from the signal w(t) as expressed by the expression (13).

$$d(t) = w(t) - l(t), l(t) = \frac{w(t-1) + w(t+1)}{2} \quad t = 1,2, \ldots, n-1 \quad (13)$$

It is known that if the difference signal d(t) between the signal w(t) and the interpolated signal l(t) is considered as a sine wave, the maximum value of the difference signal d(t) is $\sqrt{2}$ times an effective value RMS. As shown in FIG. 12C, the determining unit 601 determines the maximum value estimated from the difference signal d(t) as the threshold TH, and if the absolute value of the difference 1205 between the estimated value of the prediction of the signal w(t) and the interpolated value of the interpolated signal l(t) exceeds the threshold TH, the determining unit 601 considers the value of the difference signal d(t) as a value deviated from the sine wave, that is, a value with a large error.

In step S702, the determining unit 601 calculates $\sqrt{2}$ times the effective value RMS of the difference signals d(t) as a threshold TH, as expressed by the expression (14).

$$TH = \sqrt{2} \cdot RMS, RMS = \sqrt{\frac{1}{n-1} \cdot \sum_{t=1}^{n-1} d(t)^2} \quad t = 1,2, \ldots, n-1 \quad (14)$$

Here, the determining unit 601 calculates the threshold TH using the effective value RMS, but the method for calculating the threshold TH is not limited thereto. For example, the determining unit 601 may calculate the threshold TH using the median of the sum of squares of the difference signals d(t) instead of the effective value RMS. In this case, the determining unit 601 can set a threshold value TH that is more robust to an outlier than the effective value RMS.

In step S703, the determining unit 601 determines whether the absolute value of the difference between the estimated value V of the signal w(t) and the interpolated value of the interpolated signal l(t) exceeds the threshold value TH. If the absolute value of the difference exceeds the threshold value TH, since the estimated value V is not valid, the process proceeds to step S704. If the absolute value of the difference does not exceed the threshold value TH, the estimated value V is valid, and the process of the flowchart of FIG. 7 ends.

In step S704, the modifying unit 602 corrects the estimated value V. Specifically, if the value obtained by subtracting the interpolated value l(n) from the estimated value V is larger than the threshold value TH, the modifying unit 602 updates the value Vc obtained by adding the threshold value TH to the interpolated value l(n) as a new estimated value V as expressed by the expression (15). If the value obtained by subtracting the interpolated value l(n) from the estimated value V is smaller than the threshold value −TH, the modifying unit 602 updates the value Vc obtained by subtracting the threshold value TH from the interpolation value l(n) as the new estimated value V as expressed by the expression (15). If the absolute value of the difference between the estimated value V and the interpolated value l(n) is equal to or smaller than the threshold value TH, the modifying unit 602 does not correct the estimated value V.

$$V_C = \begin{cases} l(n) + TH, & V - l(n) > TH \\ l(n) - TH, & V - l(n) < -TH \end{cases} \quad (15)$$

13

14

As described above, in step S208 in FIG. 2, the first correcting unit 116 calculates the estimated value of the second defect pixel 1102 using the values of the second pixel group 1106. In step S209, the second correcting unit 117 calculates the estimated values V1 and V2 of the first defect pixel 1006 using the values of the first pixel groups 1008 and 1009.

In step S702 in FIG. 7, with respect to the first correcting unit 116, the determining unit 601 calculates a second threshold TH based on difference signals d(t) between the values of the second pixel group 1106 interpolated based on the values of the second pixel group 1106 and the values of the second pixel group 1106. Further, with respect to the second correcting unit 117, the determining unit 601 calculates a first threshold TH based on a difference signals d(t) between the values of the first pixel group 1008 interpolated based on the values of the first pixel group 1008 and the values of the first pixel group 1008.

In step S703, with respect to the first correcting unit 116, if the absolute value of the difference between the interpolated value of the second defect pixel 1102 based on the values of the second pixel group 1106 and the estimated value of the second defect pixel 1102 is larger than the second threshold value TH, the determining unit 601 advances the processing to step S704. That is, the determining unit 601 determines that the estimated value of the second defect pixel 1102 is not valid.

Further, with respect to the second correcting unit 117, if the absolute value of the difference between the interpolated value of the first defect pixel 1006 based on the values of the first pixel group 1008 and the estimated value V1 of the first defect pixel 1006 is larger than the first threshold TH, the determining unit 601 advances the processing to step S704. That is, the determining unit 601 determines that the estimated value V1 of the first defect pixel 1006 is not valid.

In step S704, with respect to the first correcting unit 116, if it is determined that the estimated value of the second defect pixel 1102 is not valid, the modifying unit 602 modifies the estimated value of the second defect pixel 1102 so that the absolute value of the estimated value of the second defect pixel 1102 becomes the second threshold TH. In this case, the modifying unit 602 may modify the estimate of the second defect pixel 1102 to the interpolated value of the second defect pixel 1102.

With respect to the second correcting unit 117, if it is determined that the estimated value V1 of the first defect pixel 1006 is not valid, the modifying unit 602 modifies the estimated value of the first defect pixel 1006 so that the absolute value of the estimated value V1 of the first defect pixel 1006 becomes the first threshold TH. In this case, the modifying unit 602 may modify the estimated value V1 of the first defect pixel 1006 to the interpolated value of the first defect pixel 1006.

As described above, according to the second embodiment, the image processing apparatus 112 determines the validity of the estimated value V of the prediction, and modifies the estimated value V. Therefore, the correction can be performed with high accuracy even if the prediction error is large.

According to the first and second embodiments of the present disclosure, in the correction of the value of the defect pixel using the prediction analysis, even if the defect pixels are densely packed, the correction can be performed with high accuracy.

Other Embodiment

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-145495, filed Sep. 7, 2021 which is hereby incorporated by reference herein in its entirety.

What is claimed is:

1. An image processing apparatus comprising:
at least one processor; and
at least one memory having stored thereon instructions which, when executed by the at least one processor, cause the image processing apparatus at least to:
correct, in a case where a first pixel group continuing to a first defect pixel in an image includes a second defect pixel, a value of the second defect pixel by using values of a second pixel group continuing to the second defect pixel, and calculate an estimated value of the second defect pixel by using the values of the second pixel group;
correct a value of the first defect pixel by using values of the first pixel group including a corrected value of the second defect pixel, and calculate an estimated value of the first defect pixel by using the values of the first pixel group;
determine that the estimated value of the second defect pixel is not valid in a case where an absolute value of a difference between an interpolated value of the second defect pixel based on the values of the second pixel group and the estimated value of the second defect pixel is larger than a second threshold; and
determine that the estimated value of the first defect pixel is not valid in a case where an absolute value of a difference between an interpolated value of the first defect pixel based on the values of the first pixel group and the estimated value of the first defect pixel is larger than a first threshold.

2. The image processing apparatus according to claim 1, wherein the image is an image captured using a radiation detector.

3. The image processing apparatus according to claim 1, wherein the value of the first defect pixel and the value of the second defect pixel are corrected by interpolation.

4. The image processing apparatus according to claim 1, wherein the instructions, when executed by the at least one processor, further cause the image processing apparatus at least to:

select, as the first pixel group, a pixel group continuing to the first defect pixel in any one of a row direction, a column direction, and a diagonal direction.

5. The image processing apparatus according to claim 1, wherein the instructions, when executed by the at least one processor, further cause the image processing apparatus at least to:

select, as the first pixel group, a pixel group in a direction in which a number of defect pixels existing in the pixel group is smaller between a pixel group continuing to the first defect pixel present in a row direction and a pixel group continuing to the first defect pixel in a column direction.

6. The image processing apparatus according to claim 1, wherein the value of the second defect pixel is corrected using values of a second pixel group continuing to the second defect pixel in a direction opposite to a direction in which the first defect pixel exists with respect to the second defect pixel.

7. The image processing apparatus according to claim 1, wherein in a case where a plurality of second defect pixels exists in the first pixel group, the values of the second defect pixels are corrected sequentially in order from a second defect pixel farther from the first defect pixel among the plurality of second defect pixels.

8. The image processing apparatus according to claim 1, wherein the instructions, when executed by the at least one processor, further cause the image processing apparatus at least to:

select two or more first pixel groups; and calculate two or more estimated values of the first defect pixel by using values of the two or more first pixel groups, wherein the value of the first defect pixel is corrected based on the two or more estimated values.

9. The image processing apparatus according to claim 8, wherein the value of the first defect pixel is corrected from a value based on an average value or an order statistic of the two or more estimated values.

10. The image processing apparatus according to claim 1, wherein the instructions, when executed by the at least one processor, further cause the image processing apparatus at least to:

remove a trend from the values of the second pixel group and the values of the first pixel group, wherein the value of the first defect pixel and the value of the second defect pixel are corrected using values from which the trend is removed.

11. The image processing apparatus according to claim 10, wherein the removing of the trend includes a process of approximating the values of the first pixel group or the second pixel group by a polynomial and subtracting an approximate value from the values of the first pixel group or the second pixel group.

12. The image processing apparatus according to claim 1, wherein the instructions, when executed by the at least one processor, further cause the image processing apparatus at least to:

calculate the second threshold based on a difference between values of an interpolated second pixel group and the values of the second pixel group, wherein the interpolated second pixel group is based on the values of the second pixel group; and calculate the first threshold based on a difference between values of an interpolated first pixel group and the values of the first pixel group, wherein the interpolated first pixel group is based on the values of the first pixel group.

13. The image processing apparatus according to claim 1, wherein the instructions, when executed by the at least one processor, further cause the image processing apparatus at least to:

modify, in a case where it is determined that the estimated value of the second defect pixel is not valid, the estimated value of the second defect pixel to the interpolated value of the second defect pixel or modify the estimated value of the second defect pixel so that an absolute value of the estimated value of the second defect pixel becomes the second threshold value, and in a case where it is determined that the estimated value of the first defect pixel is not valid, modify the estimated value of the first defect pixel to the interpolated value of the first defect pixel or modify the estimated value of the first defect pixel so that an absolute value of the estimated value of the first defect pixel becomes the first threshold value.

14. A radiation imaging system comprising:

the image processing apparatus according to claim 1; and a radiation detector arranged to capture the image.

15. The image processing apparatus according to claim 1, wherein the value of the second defect pixel is corrected by using the values of the second pixel group based on a prediction analysis, and the value of the first defect pixel is corrected based on a prediction analysis by using the values of the first pixel group including the corrected value of the second defect pixel.

16. The image processing apparatus according to claim 15, wherein each of the prediction analyses is a prediction analysis including an autoregressive model for predicting an unknown value by a linear map using a known value.

17. An image processing method of an image processing apparatus, the image processing method comprising:

correcting, in a case where a first pixel group continuing to a first defect pixel in an image includes a second defect pixel, a value of the second defect pixel by using values of a second pixel group continuing to the second defect pixel, and calculate an estimated value of the second defect pixel by using the values of the second pixel group;

correcting a value of the first defect pixel by using values of the first pixel group including a corrected value of the second defect pixel, and calculating an estimated value of the first defect pixel by using the values of the first pixel group; and determining that the estimated value of the second defect pixel is not valid in a case where an absolute value of a difference between an interpolated value of the second defect pixel based on the values of the second pixel group and the estimated value of the second defect pixel is larger than a second threshold; and determining that the estimated value of the first defect pixel is not valid in a case where an absolute value of a difference between an interpolated value of the first defect pixel based on the values of the first pixel group and the estimated value of the first defect pixel is larger than a first threshold.

18. A non-transitory computer-readable medium having stored thereon a program that, when executed by a computer, causes the computer to perform the respective steps of the image processing method according to claim 17.

\* \* \* \* \*